(12) United States Patent
Edwards et al.

(10) Patent No.: US 7,902,224 B2
(45) Date of Patent: Mar. 8, 2011

(54) TETRAHYDRO-NAPHTHALENE DERIVATIVES AS GLUCOCORTICOID RECEPTOR MODULATORS

(75) Inventors: Christine Edwards, Harlow (GB); Garry Fenton, Harlow (GB); Simon John Fawcett MacDonald, Stevenage (GB); Gordon Gad Weingarten, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 975 days.

(21) Appl. No.: 11/573,301

(22) PCT Filed: Aug. 10, 2005

(86) PCT No.: PCT/EP2005/008763
§ 371 (c)(1),
(2), (4) Date: Feb. 6, 2007

(87) PCT Pub. No.: WO2006/015870
PCT Pub. Date: Feb. 16, 2006

(65) Prior Publication Data
US 2007/0224130 A1 Sep. 27, 2007

(30) Foreign Application Priority Data
Aug. 12, 2004 (GB) .................................. 0418045.1

(51) Int. Cl.
*C07D 215/04* (2006.01)
*A61K 31/47* (2006.01)
(52) U.S. Cl. .......... 514/310; 514/311; 546/143; 546/171
(58) Field of Classification Search .................. None
See application file for complete search history.

(56) References Cited

FOREIGN PATENT DOCUMENTS

| DE | 10261874 A1 | 7/2004 |
|---|---|---|
| EP | 0439265 | 7/1991 |
| WO | 0032584 A2 | 6/2000 |
| WO | WO 00/34243 | 6/2000 |
| WO | 0142193 A1 | 6/2001 |
| WO | 0210143 A1 | 2/2002 |
| WO | 02066422 A1 | 8/2002 |
| WO | 02070490 A1 | 9/2002 |
| WO | 02076933 A1 | 10/2002 |
| WO | 03024439 A1 | 3/2003 |
| WO | 03042160 A1 | 5/2003 |
| WO | 03072539 A1 | 9/2003 |
| WO | 03082280 A1 | 10/2003 |
| WO | WO 03/082827 | 10/2003 |
| WO | 03091204 A1 | 11/2003 |
| WO | 2004016578 A2 | 2/2004 |
| WO | 2004022547 A1 | 3/2004 |
| WO | 2004037768 A2 | 5/2004 |
| WO | 2004037773 A1 | 5/2004 |
| WO | 2004037807 A2 | 5/2004 |
| WO | 2004039762 A1 | 5/2004 |
| WO | 2004039766 A1 | 5/2004 |
| WO | WO 2004/063163 | 7/2004 |
| WO | WO 2004/071389 | 8/2004 |
| WO | 2005003098 A1 | 1/2005 |
| WO | 2005030213 A1 | 4/2005 |
| WO | 2005044354 A1 | 5/2005 |

OTHER PUBLICATIONS

Allen, D.B.; Do intranasal cortisosteriods affect childhood growth?; Allergy; 2000; 62; 15-18.
Andrews, et al.; Glucocorticoids and insulin resistance: old hormones, new targets; Clinical Science; 1999; 96; 513-523.
Austin et al; Mometasone furoate is a less specific glucocorticoid than fluticasone propionate; European Respiratory Journal; 2002; 20; 1386-1392.
Barnes and Adcock; Anti-inflammatory actions of steroids: molecular mechanisms; TiPS; Dec. 1993; 14; 436-441.
Cato and Wade; Molecular mechanisms of anti-inflammatory action of glucocorticoids; BioEssays; 1996; 18/5; 371-378.
Cumming et al; Use of inhaled corticosteroids and the risk of cataracts; The New England Journal of Medicine; 1997; 337/1; 8-14.
Faul et al; High dose inhaled corticosteroids and dose dependent loss of diabetic control; BMJ; 1998; 317; 1491.
Fujii et al; Novel phosphodiesterase 4 inhibitor T-440 reverses and prevents human bronchial contraction induced by allergen; The Journal of Pharmacology and Experimental Therapeutics; 1998; 28/1; 162-169.
Hartley and McKiernan; Titanium reagents for the alkylidenation of carboxylic acid and carbonic acid derivates; Journal of the Chemical Society—Perkin Transactions I; 2002; 2763-2793.
Hibino et al; Carbonyl methylenation of easily enolizable ketones; Tetrahedron Letters; 1985; 26/45; 5579-5580.

(Continued)

*Primary Examiner* — Zinna N Davis
(74) *Attorney, Agent, or Firm* — Robert J. Smith

(57) ABSTRACT

The present invention is directed to compounds of formula (I):

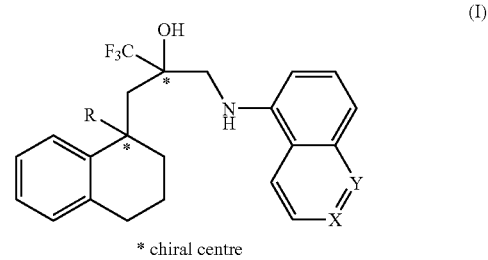

(I)

* chiral centre wherein
R represents a methyl or an ethyl group
X represents N, C—H or C—CH$_3$
when X represents C—H or C—CH$_3$, Y represents N
when X represents N, Y represents C—H
and physiologically functional derivatives thereof, pharmaceutical compositions comprising the compounds, the use of the compounds for the manufacture of medicaments particularly for the treatment of inflammatory and/or allergic conditions, processes for the preparation of the compounds, and chemical intermediates in the processes for the manufacture of the compounds.

20 Claims, No Drawings

OTHER PUBLICATIONS

Pauwels et al; Long-term treatment with inhaled budesonide in persons with mild chronic obstructive pulmonary disease who continue smoking; The New England Journal of Medicine; 1999; 340/25; 1948-1953.

Ray et al; Anti-inflammation: Direct physical association and functional antagonism between transcription factor NF-KB and the glucocorticoid receptor; Chest; 1995; 107/3; 139S.

Ray et al; Induction of the e-selection promoter by interleukin 1 and tumor necrosis factor a, and inhibition by glucocorticoids; Journal of Biochemistry; 1997; 320; 707-715.

Schacke et al; Mechanisms involved in the side effects of glucocorticoids; Pharmacology & Therapeutics; 2002; 96; 23-43.

Wong et al; Inhaled corticosteroid use and bone-mineral density in patients with asthma; The Lancet; 2000; 335; 1399-1403.

Elinson et al; Electrocatalytic transformation of malononitrile and cycloalkylidenemalononitriles into spirobycyclic and spirotricyclic compounds containing 1,1,2,2-tetracyanocyclopropane fragment; Russian Chemical Bulletin; 2003; 52/10; 2235-2240.

Database Beilstein, Beilstein Institute for Organic Chemistry, Frankfurt-Main, DE, XP002358363, BRN: 1961178, abstract.

Sole et al., "Intramolecular pd-mediated processes of amino-tethered aryl halides and ketones: Insight into the ketone.alpha.-arylation and carbonyl-addition dichotomy. A new class of four-membered azapalladacycles," *Journal of the American Chemical Society* 125(6):1587-1594 (2003).

TETRAHYDRO-NAPHTHALENE DERIVATIVES AS GLUCOCORTICOID RECEPTOR MODULATORS

CROSS-REFERENCE TO RELATED APPLICATIONS

This application is filed pursuant to 35 U.S.C. §371 as a United States National Phase Application of International Application No. PCT/EP2005/008763 filed 10 Aug. 2005, which claims priority from Great Britain Application No. 0418045.1 filed 12 Aug. 2004.

The present invention relates to compounds which are non-steroidal glucocorticoid receptor modulators, pharmaceutical compositions comprising the compounds, the use of the compounds for the manufacture of medicaments particularly for the treatment of inflammatory and/or allergic conditions, processes for the preparation of the compounds, and chemical intermediates in the processes for the manufacture of the compounds.

Nuclear receptors are a class of structurally related proteins involved in the regulation of gene expression. The steroid hormone receptors are a subset of this family whose natural ligands typically comprise endogenous steroids such as estradiol (estrogen receptor), progesterone (progesterone receptor) and cortisol (glucocorticoid receptor). Man-made ligands to these receptors play an important role in human health, in particular the use of glucocorticoid agonists to treat a wide range of inflammatory conditions.

Glucocorticoids exert their actions at the glucocorticoid receptor (GR) through at least two intracellular mechanisms, transactivation and transrepression (see: Schacke, H, Docke, W-D. & Asadullah, K (2002) *Pharmacol and Therapeutics* 96: 23-43; Ray, A., Siegel, M. D., Prefontaine, K. E. & Ray, P. (1995) *Chest* 107: 139S; and Konig, H., Ponta, H., Rahmsdorf, H. J. & Herrlich, P. (1992) *EMBO J* 11: 2241-2246). Transactivation involves direct binding of the glucocorticoid receptor to distinct deoxyribonucleic acid (DNA) response elements (GREs) within gene promoters, usually but not always increasing the transcription of the downstream gene product. Recently, it has been shown that the GR can also regulate gene expression through an additional pathway (transrepression) in which the GR does not bind directly to DNA. This mechanism involves interaction of the GR with other transcription factors, in particular NFkB and AP1, leading to inhibition of their pro-transcriptional activity (Schacke, H, Docke, W-D. & Asadullah, K (2002) *Pharmacol and Therapeutics* 96: 23-43; and Ray, A., Siegel, M. D., Prefontaine, K. E. & Ray, P. (1995) *Chest* 107: 139S). Many of the genes involved in the inflammatory response are transcriptionally activated through the NFkB and AP1 pathways and therefore inhibition of this pathway by glucocorticoids may explain their anti-inflammatory effect (see: Barnes, P. J. & Adcock, I. (1993) *Trend Pharmacol Sci* 14: 436-441; and Cato, A. C. & Wade, E. (1996) *Bioessays* 18: 371-378).

Despite the effectiveness of glucocorticoids in treating a wide range of conditions, a number of side-effects are associated with pathological increases in endogenous cortisol or the use of exogenous, and particularly systemically administered, glucocorticoids. These include reduction in bone mineral density (Wong, C. A., Walsh, L. J., Smith, C. J. et al. (2000) *Lancet* 355: 1399-1403), slowing of growth (Allen, D. B. (2000) *Allergy* 55: suppl 62, 15-18), skin bruising (Pauwels, R. A., Lofdahl, C. G., Latinen, L. A. et al. (1999) *N Engl J Med* 340: 1948-1953), development of cataracts (Cumming, R. G., Mitchell, P. & Leeder, S. R. (1997) *N Engl J Med* 337: 8-14) and dysregulation of lipid and glucose metabolism (Faul, J. L., Tormey, W., Tormey, V. & Burke, C. (1998) *BMJ* 317: 1491; Andrews, R. C. & Walker, B. R. (1999) *Clin Sci* 96: 513-523). The side-effects are serious enough often to limit the dose of glucocorticoid that can be used to treat the underlying pathology leading to reduced efficacy of treatment.

It has been suggested that excessive activation of the transactivation-GRE pathway may mediate some of these side-effects (see Schacke, H, Docke, W-D. & Asadullah, K (2002) *Pharmacol and Therapeutics* 96: 23-43). Development of glucocorticoids that selectively modulate the transrepression pathway compared with the transactivation pathway may therefore have a superior anti-inflammatory to side-effect therapeutic index, allowing more effective and safer treatment of the patient. This new class of glucocorticoids could be used to treat more effectively and more safely the whole spectrum of disease currently treated by current glucocorticoids.

Current known glucocorticoids have proved useful in the treatment of inflammation, tissue rejection, auto-immunity, various malignancies, such as leukemias and lymphomas, Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia and Little's syndrome.

Glucocorticoids are especially useful in disease states involving systemic inflammation such as inflammatory bowel disease, systemic lupus erythematosus, polyarteritis nodosa, Wegener's granulomatosis, giant cell arteritis, rheumatoid arthritis, osteoarthritis, seasonal rhinitis, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoids have also been used as immunostimulants and repressors and as wound healing and tissue repair agents.

Glucocorticoids have also found use in the treatment of diseases such as inflammatory scalp alopecia, panniculitis, psoriasis, discoid lupus erythemnatosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform and cutaneous T-cell lymphoma.

WO00/32584, WO02/10143, WO03/082827, WO/03082280, DE10261874, WO05/003098 and WO05/030213 disclose certain non-steroidal glucocorticoid receptor modulators.

The present invention provides compounds of formula (I):

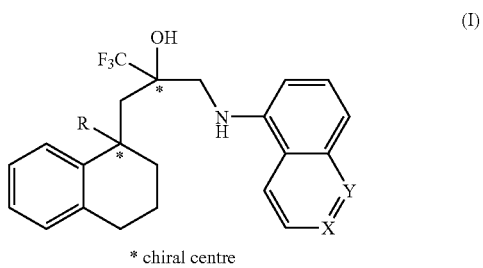

(I)

* chiral centre wherein

R represents a methyl or an ethyl group

X represents N, C—H or C—CH$_3$ when X represents C—H or C—CH$_3$, Y represents N when X represents N, Y represents C—H and physiologically functional derivatives thereof (hereinafter "the compounds of the invention").

In one embodiment of the invention R represents methyl. In a second embodiment of the invention R represents ethyl.

In another embodiment of the invention X represents C—H and Y represents N. In a further embodiment of the invention X represents C—CH$_3$ and Y represents N.

In another embodiment of the invention X represents N and Y represents C—H.

The compounds of formula (I) each contain two chiral centres and there are four possible stereoisomers of each compound of formula (I). Further, at least one of the possible stereoisomers of each compound of formula (I) modulates the glucocorticoid receptor.

The terms D1 and D2 are used herein to refer to the diastereomers of a compound of formula (I), based on the order of their elution using the chromatography methodology described herein (LCMS). D1 refers to the first diastereomer to elute, and D2 refers to the second diastereomer to elute.

The terms D1E1, D1E2, D2E1 and D2E2 are used herein to refer to the isomers of a compound of formula (I). D1E1 refers to the first enantiomer to elute, and D1E2 refers to the second enantiomer to elute, during chiral separation of diastereomer D1 according to the methodology described herein. D2E1 refers to the first enantiomer to elute, and D2E2 refers to the second enantiomer to elute, during chiral separation of diastereomer D2 according to the methodology described herein.

It will be appreciated by those skilled in the art that although the absolute retention time on chromatography can be variable, the order of elution remains the same when the same column and conditions are employed. However, the use of a different chromatography column and conditions may alter the order of elution.

A mixture of isomers, such as a racemic mixture, may be preferred, for example, a mixture of all four isomers, or a racemic mixture of two isomers may be preferred, for example diastereomer D1. Thus, in one embodiment of the invention the compound of formula (I) is the diastereomer D1.

Alternatively, a single isomer may be preferred, for example the isomer D1E1 or the isomer D1E2. Therefore, in one embodiment of the invention the compound of formula (I) is the enantiomer D1E1. In another embodiment of the invention the compound of formula (I) is the enantiomer D1E2.

When the group R represents ethyl, X represents C—CH$_3$ and Y represents N, preferably the compound is diastereomer D1. Diastereomer D1 is characterised by having a retention time of about 3.07 min when eluted using the chromatography methodology described herein (LCMS). For comparative purposes, diastereomer D2 has a retention time of about 3.11 min under the same conditions. Especially preferred is the isomer D1E1, which is characterised by having a retention time of about 4.77 min when eluted on an analytical chiral HPLC on a 25×0.46 cm Chiralcel OJ column using a mobile phase of 15% ethanol in heptane at 1 mL/min. Isomer D1E1 is the earlier running enantiomer of the racemic mixture of isomers D1E1 and D1E2.

Compounds of the invention which are of particular interest include:

1,1,1-Trifluoro-3-(1-methyl-1,2,3,4-tetrahydro-1-naphthalenyl)-2-[(5-quinolinylamino) methyl]-2-propanol D1;

1,1,1-Trifluoro-3-[(2-methyl-5-quinolinyl)amino]-2-[(1-methyl-1,2,3,4-tetrahydro-1-naphthalenyl)methyl]-2-propanol D1;

1,1,1-Trifluoro-3-(5-isoquinolinylamino)-2-[(1-methyl-1,2,3,4-tetrahydro-1-naphthalenyl) methyl]-2-propanol D1;

3-(1-Ethyl-1,2,3,4-tetrahydro-1-naphthalenyl)-1,1,1-trifluoro-2-[(5-isoquinolinylamino) methyl]-2-propanol D1;

3-(1-Ethyl-1,2,3,4-tetrahydro-1-naphthalenyl)-1,1,1-trifluoro-2-{[(2-methyl-5-quinolinyl) amino]methyl}-2-propanol D1;

3-(1-Ethyl-1,2,3,4-tetrahydro-1-naphthalenyl)-1,1,1-trifluoro-2-{[(2-methyl-5-quinolinyl) amino]methyl}-2-propanol D1E1;

3-(1-Ethyl-1,2,3,4-tetrahydro-1-naphthalenyl)-1,1,1-trifluoro-2-[(5-quinolinylamino)methyl]-2-propanol D1; and physiologically functional derivatives thereof.

Compounds of the invention which are of more particular interest include:

1,1,1-Trifluoro-3-(1-methyl-1,2,3,4-tetrahydro-1-naphthalenyl)-2-[(5-quinolinylamino) methyl]-2-propanol D1E1;

1,1,1-Trifluoro-3-[(2-methyl-5-quinolinyl)amino]-2-[(1-methyl-1,2,3,4-tetrahydro-1-naphthalenyl)methyl]-2-propanol D1E1;

1,1,1-Trifluoro-3-(5-isoquinolinylamino)-2-[(1-methyl-1,2,3,4-tetrahydro-1-naphthalenyl) methyl]-2-propanol D1E2;

3-(1-Ethyl-1,2,3,4-tetrahydro-1-naphthalenyl)-1,1,1-trifluoro-2-[(5-isoquinolinylamino) methyl]-2-propanol D1E2;

3-(1-Ethyl-1,2,3,4-tetrahydro-1-naphthalenyl)-1,1,1-trifluoro-2-{[(2-methyl-5-quinolinyl) amino]methyl}-2-propanol D1E1; and physiologically functional derivatives thereof.

Compounds of the invention which are of most particular interest include:

1,1,1-Trifluoro-3-[(2-methyl-5-quinolinyl)amino]-2-[(1-methyl-1,2,3,4-tetrahydro-1-naphthalenyl)methyl]-2-propanol D1E1;

1,1,1-Trifluoro-3-(5-isoquinolinylamino)-2-[(1-methyl-1,2,3,4-tetrahydro-1-naphthalenyl) methyl]-2-propanol D1E2; and physiologically functional derivatives thereof.

The compounds of the invention may provide agonism of the glucocorticoid receptor.

It has been found that at least one of the possible stereoisomers of each of the compounds of formula (I) binds to the glucocorticoid receptor. Further, it appears that at least one of the possible stereoisomers of each of the compounds of formula (I) has glucocorticoid receptor agonist activity. Additionally, it appears that at least one of the possible stereoisomers of each of the compounds of formula (I) possesses advantageous selectivity in respect of maintaining transrepression activity whilst reducing the transactivation activity. These observations are believed to be indicative that the compounds of the invention may provide anti-inflammatory properties with fewer or less severe related side effects.

It will be appreciated by those skilled in the art that at least one isomer (e.g. an enantiomer in a diastereomer) has the described activity. The other isomers may have similar activity, less activity, no activity or may have some antagonist activity in a functional assay.

The invention includes physiologically functional derivatives of the compounds of formula (I). By the term "physiologically functional derivative" is meant a chemical derivative of a compound of formula (I) having the same physiological function as the free compound of formula (I), for example, by being convertible in the body thereto and includes any pharmaceutically acceptable esters, carbonates and carbamates, solvates of compounds of formula (I) and solvates of any pharmaceutically acceptable esters, carbonates and carbamates or salts of compounds of formula (I), which, upon administration to the recipient, are capable of providing (directly or indirectly) compounds of formula (I) or active metabolite or residue thereof.

Solvates of the compounds of formula (I) and physiologically functional derivatives thereof which are suitable for use in medicine are those wherein the associated solvent is pharmaceutically acceptable. However, solvates having non-pharmaceutically acceptable counter-ions or associated solvents are within the scope of the present invention, for example, for use as intermediates in the preparation of other compounds of formula (I) and their pharmaceutically acceptable salts, solvates, and physiologically functional derivatives.

Examples of solvates include hydrates.

The compounds of the invention are expected to have potentially beneficial anti-inflammatory or anti-allergic effects, particularly upon topical administration, demonstrated by, for example, their ability to bind to the glucocorticoid receptor and to illicit a response via that receptor. Hence, the compounds of the invention may be useful in the treatment of inflammatory and/or allergic disorders.

Examples of disease states in which the compounds of the invention are expected to have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease (COPD), interstitial lung disease, and fibrosis; inflammatory bowel conditions such as ulcerative colitis and Crohn's disease; and auto-immune diseases such as rheumatoid arthritis.

It will be appreciated by those skilled in the art that reference herein to treatment extends to prophylaxis as well as the treatment of established conditions.

As mentioned above, compounds of the invention are expected to be of use in human or veterinary medicine, in particular as anti-inflammatory and anti-allergic agents.

There is thus provided as a further aspect of the invention a compound of the invention for use in human or veterinary medicine, particularly in the treatment of patients with inflammatory and/or allergic conditions, such as rheumatoid arthritis, asthma, COPD, allergy or rhinitis.

In a further aspect of the invention a compound of the invention for use in human or veterinary medicine, particularly in the treatment of patients with skin disease such as eczema, psoriasis, allergic dermatitis, neurodermatitis, pruritis and hypersensitivity reactions.

According to another aspect of the invention, there is provided the use of a compound of the invention for the manufacture of a medicament for the treatment of patients with inflammatory and/or allergic conditions, such as rheumatoid arthritis, asthma, COPD, allergy or rhinitis.

According to yet to another aspect of the invention, there is provided the use of a compound of the invention for the manufacture of a medicament for the treatment of patients with skin disease such as eczema, psoriasis, allergic dermatitis, neurodermatitis, pruritis and hypersensitivity reactions.

In a further or alternative aspect, there is provided a method for the treatment of a human or animal subject with an inflammatory and/or allergic condition, which method comprises administering to said human or animal subject an effective amount of a compound of the invention.

In yet a further or alternative aspect, there is provided a method for the treatment of a human or animal subject with for skin diseases such as eczema, psoriasis, allergic dermatitis, neurodermatitis, pruritis and hypersensitivity reactions, which method comprises administering to said human or animal subject an effective amount of a compound of the invention.

The compounds according to the invention may be formulated for administration in any convenient way, and the invention therefore also includes within its scope pharmaceutical compositions comprising a compound of the invention together, if desirable, in admixture with one or more physiologically acceptable diluents or carriers.

Further, there is provided a process for the preparation of such pharmaceutical compositions which comprises mixing the ingredients.

The compounds of the invention may, for example, be formulated for oral, buccal, sublingual, parenteral, local rectal administration or other local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Formulations for administration topically to the nose for example, for the treatment of rhinitis, include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of the invention may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

In one embodiment there is provided a pharmaceutical aerosol formulation comprising a compound of formula (I) and a fluorocarbon or hydrogen-containing chlorofluorocarbon as propellant, optionally in combination with a surfactant and/or cosolvent.

In another embodiment is provided a pharmaceutical formulation wherein the propellant is selected from 1,1,1,2-tetrafluoroethane, 1,1,1,2,3,3,3-heptafluoro-n-propane and mixtures thereof.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 μg-10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably from 0.01 to 0.5%. However, in powders for inhalation or insufflation the proportion used will be within the range of from 0.1 to 5%.

Aerosol formulations are preferably arranged so that each metered dose or "puff" of aerosol contains from 20 μg to 10 mg preferably from 20 μg to 2000 μg, more preferably about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg preferably, from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particular (e.g., micronised) drug should be such as to permit inhalation of substantially all the drug into the lungs upon administration of the aerosol formulation and will thus be less than 100 microns, desirably less than 20 microns, and, in particular, in the range of from 1 to 10 microns, such as from 1 to 5 microns, more preferably from 2 to 3 microns.

The formulations of the invention may be prepared by dispersal or dissolution of the medicament and a compound of the invention in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO/96/32099). Preferably the canister is fitted with a cap assembly, wherein a drug-metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold to ensure formulation does not vaporise, and then a metering valve crimped onto the canister.

Typically, in batches prepared for pharmaceutical use, each filled canister is check-weighed, coded with a batch number and packed into a tray for storage before release testing.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

The compounds according to the invention may in general be given by internal administration in cases where systemic adreno-cortical therapy is indicated.

Slow release or enteric coated formulations may be advantageous, particularly for the treatment of inflammatory bowel disorders.

In some embodiments, the compound of formula (I) will be formulated for oral administration. In other embodiments the compounds of formula (I) will be formulated for inhaled administration.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example another corticosteroid or an NSAID), an anticholinergic agent, a 2-adrenoreceptor agonist, an antiinfective agent (e.g. an antibiotic or an antiviral), or an antihistamine. One embodiment of the invention encompasses combinations comprising a compound of formula (I) or a pharmaceutically acceptable salt, solvate or physiologically functional derivative thereof together with a $\beta_2$-adrenoreceptor agonist, and/or an anticholinergic, and/or a PDE-4 inhibitor. Suitable combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable combinations include combinations comprising a compound of the invention together with a $\beta_2$-adrenoreceptor agonist.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, those having a therapeutic effect over a 24 hour period such as salmeterol or formoterol.

Examples of long acting $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Suitable long-acting $\beta_2$-adrenoreceptor agonists include compounds of formula (XX):

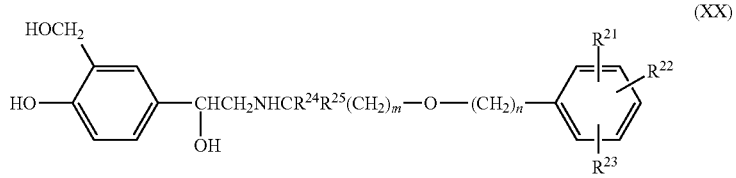

(XX)

or a salt or solvate thereof, wherein:
m is an integer of from 2 to 8;
n is an integer of from 3 to 11,
with the proviso that m+n is 5 to 19,
$R^{21}$ is $-XSO_2NR^{26}R^{27}$ wherein X is $-(CH_2)_p$- or $C_{2-6}$ alkenylene;
$R^{26}$ and $R^{27}$ are independently selected from hydrogen, $C_{1-6}$alkyl, $C_{3-7}$cycloalkyl, $C(O)NR^{28}R^{29}$, phenyl, and phenyl ($C_{1-4}$alkyl)-, or $R^{26}$ and $R^{27}$, together with the nitrogen to which they are bonded, form a 5-, 6-, or 7-membered nitrogen containing ring, and $R^{26}$ and $R^{27}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{28}$, —$SO_2NR^{28}R^{29}$, —$CONR^{28}R^{29}$, —$NR^{28}C(O)R^{29}$, or a 5-, 6- or 7-membered heterocylic ring;
$R^{28}$ and $R^{29}$ are independently selected from hydrogen, $C_{1-6}$alkyl, $C_{3-6}$cycloalkyl, phenyl, and phenyl ($C_{1-4}$alkyl)-; and
p is an integer of from 0 to 6, preferably from 0 to 4;
$R^{22}$ and $R^{23}$ are independently selected from hydrogen, $C_{1-6}$alkyl, $C_{1-6}$alkoxy, halo, phenyl, and $C_{1-6}$haloalkyl; and
$R^{24}$ and $R^{25}$ are independently selected from hydrogen and $C_{1-4}$alkyl with the proviso that the total number of carbon atoms in $R^{24}$ and $R^{25}$ is not more than 4.

Other examples of long-acting $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]foramide, and
N-2{2-[4-(3-phenyl-4-methoxyphenyl)aminophenyl]ethyl}-2-hydroxy-2-(8-hydroxy-2(1H)-quinolinon-5-yl)ethylamine.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (e.g. montelukast), iNOS inhibitors, tryptase and elastase inhibitors, beta-2 integrin antagonists and adenosine receptor agonists or antagonists (e.g. adenosine 2a agonists), cytokine antagonists (e.g. chemokine antagonists, such as a CCR3 antagonist) or inhibitors of cytokine synthesis, or 5-lipoxygenase inhibitors. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof. An iNOS (inducible nitric oxide synthase inhibitor) is preferably for oral administration. Suitable iNOS inhibitors include those disclosed in WO 93/13055, WO 98/30537, WO02/50021, WO 95/34534 and WO 99/62875. Suitable CCR3 inhibitors include those disclosed in WO02/26722.

Of particular interest is use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 03 Sep. 1996; this patent and the compounds it discloses are incorporated herein in full by reference.

Other compounds of interest include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO 99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*, 10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Suitable anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (e.g. as the bromide, CAS 22254-24-6, sold under the name Atrovent), oxitropium (e.g. as the bromide, CAS 30286-75-0) and tiotropium (e.g. as the bromide, CAS 136310-93-5, sold under the name Spiriva). Also of interest are revatropate (e.g. as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (e.g. as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other suitable anticholinergic agents include compounds of formula (XXI), which are disclosed in U.S. patent application 60/487,981:

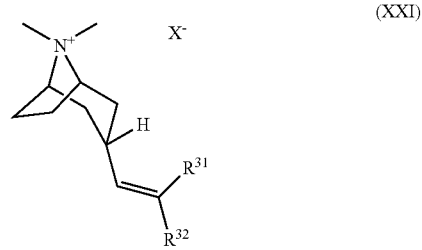

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl-groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in U.S. patent application 60/511,009:

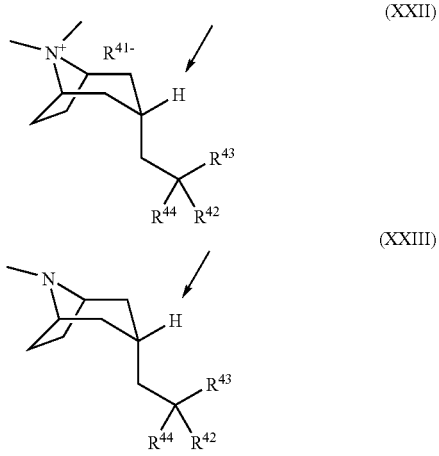

(XXII)

(XXIII)

wherein:
the H atom indicated is in the exo position;
$R^{41}$ represents an anion associated with the positive charge of the N atom. $R^{41}$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;
$R^{44}$ is slected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —CN, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, —$CH_2N(R^{48})CONH(R^{47})$;

$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:
(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo [3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol; N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

Further compounds include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;

(Endo)-3-(2-cyano-2,2-di-thiophen-2-yl-ethyl)-8,8-dimethyl-1-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, e.g diphenylhydramine, pyrilamine, clemastine, chloropheniramine. Second generation antagonists, which are non-sedating, include loratidine, desloratidine, terfenadine, astemizole, acrivastine, azelastine, levocetirizine fexofenadine and cetirizine.

Examples of anti-histamines include loratidine, desloratidine, fexofenadine and cetirizine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a $\beta_2$-adrenoreceptor agonist.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably, the individual compounds will be administered simultaneously in a combined pharmaceutical formulation. Appropriate doses of known therapeutic agents will be readily appreciated by those skilled in the art.

There are four possible isomers of compounds of formula (I). These are called isomers D1E1, D1E2, D2E1 and D2E2 herein.

For example, isomer D1E1 of the compound of formula (I) wherein the group R represents ethyl, X represents C—CH$_3$ and Y represents N is characterised in having a retention time in analytical chiral HPLC on a 25×0.46 cm Chiralcel OJ column using a mobile phase of 15% ethanol in heptane eluting at 1 mL/min of about 4.77 min. Isomer D1E2 of the compound of formula (I) wherein the group R represents ethyl, X represents C—CH$_3$ and Y represents N has a retention time of about 7.83 min under the same conditions. Isomers D2E1 and D2E2 elute at about 6.12 min and 7.30 min respectively when analysed by chiral HPLC on a 25×0.46 cm Chiralpak AD column using a mobile phase of 5% ethanol in heptane eluting at 1 mL/min.

It will be appreciated by those skilled in the art that although the absolute retention time on chiral chromatography can be variable, the order of elution of the enantiomers remains the same when the same chiral column and conditions are employed.

Preferred isomers of the compound of formula (I) may be prepared by chromatographic separation of the isomer from a mixture of enantiomeric isomers (e.g. a racemic mixture, such as a diastereomer D1).

There are also provided methods for the preparative separation of isomer D1E1 of a compound of formula (I) from a mixture of isomers D1E1 and D1E2 (e.g. a racemic mixture, such as diastereomer D1) by chromatography.

According to another aspect of the invention there is provided a mixture of isomer D1E1 of a compound of formula (I) with one or more other isomers e.g. a racemic mixture of isomers D1E1 and D1E2 (i.e. diastereomer D1).

A mixture (e.g. racemic mixture) of enantiomeric isomers D1E1 and D1E2 may be prepared by chromatographic separation from a mixture of isomers D1E1, D1E2, D2E1 and D2E2.

The invention also provides a mixture (e.g. a racemic mixture) of isomers D1E1, D1E2, D2E1 and D2E2.

A first process (A) according to the invention for the preparation of compounds of formula (I) comprises reaction of an epoxide of formula (II):

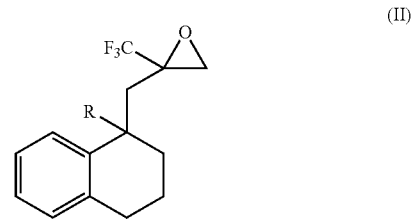

wherein R represents a methyl or an ethyl group.
with a quinolinamine or isoquinolinamine of formula (III):

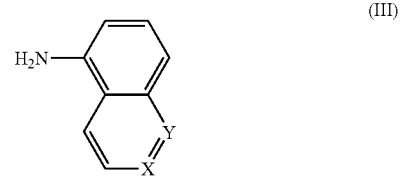

wherein X and Y are as defined above for compounds of formula (I).

The reaction will generally be performed in the presence of an inert solvent, such as N,N-dimethylformamide (DMF) and a base, such as potassium-t-butoxide, at a non-extreme temperature, for example, 0-120° C., and more suitably at room temperature.

Compounds of formula (II) may be prepared by reaction of compounds of formula (IV):

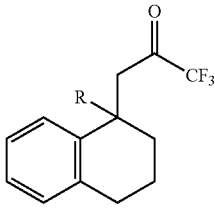

(IV)

wherein R represents a methyl or ethyl group with sulphur ylides such as dimethylsulphonium methylide or more preferably dimethyloxosulphonium methylide. The latter is conveniently generated in situ from trimethylsulphoxonium iodide and sodium hydride in DMSO.

Compounds of formula (III) are available commercially from suppliers such as Aldrich.

Compounds of formula (IV) may be prepared by oxidation of compounds of formula (V):

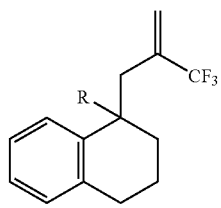

(V)

wherein R represents a methyl or ethyl group

Oxidation of compounds of formula (V) to the ketones of formula (IV) may be performed by methods detailed in "Oxidations in Organic Chemistry" M. Hudlicky, ACS, 1990 pp 77-84. Preferably ozonolysis is performed in an alcoholic solvent at a non-extreme temperature of −78 to 25° C. and worked up with a reducing agent. Preferably the ozonolysis is carried out in methanol at −78° C. and worked up with dimethyl sulphide.

Compounds of formula (V) may be prepared by coupling a compound of formula (VI):

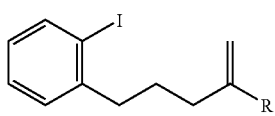

(VI)

wherein R represents a methyl or ethyl group
with a trialkyl[1-trifluomethyl)ethenyl]stannane such as the compound of formula (VII):

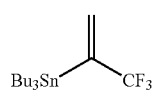

(VII)

Conversion of a compound of formula (VI) into a compound of formula (V) may be performed using a palladium derivative as catalyst, a phosphine derivative as a ligand and a trialkyl[1-trifluomethyl)ethenyl]stannane in the presence of a copper(I) salt in an inert solvent at a non-extreme temperature of 25-150° C. The preferred conditions are palladium acetate, triphenyl phosphine, tri-n-butyl[1-trifluomethyl)ethenyl] stannane (VII), copper(I) iodide in N,N-dimethyl formamide at 110° C. Analogues of compounds of formula (VI) may also be employed in which the iodine is replaced with another leaving group e.g. bromine or triflate.

Compounds of formula (VI) may be prepared from compounds of formula (VIII):

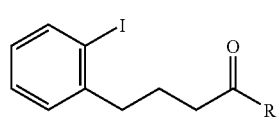

(VIII)

wherein R represents a methyl or ethyl group.

Suitable olefinating reagents include Wittig reagents, for example methyltriphenylphosphonium salts. Peterson, Tebbe, Petasis and Lombardo reagents are also suitable. Reactions of this type are described in further detail in: R. C. Hartley et al., *J Chem Soc, Perkin Trans* 1 (2002) 2763-2793 and *Tetrahedron Lett* (1985) 26: 5579-5580. Preferably a Wittig reaction on compound (VIII) may be carried out in a polar solvent such as diethylether, tetrahydrofuran, ethylene glycol, dimethylether, diglyme or dioxane, in the presence of a strong base, for example n-BuLi, sec-BuLi, t-BuLi, LDA, LiHMDS, NaHMDS, KHMDS, NaH or KO'BU, at a temperature in the range of −78° C. to +70° C. Preferably, a Wittig reaction is carried out using methyltriphenyphosphonium bromide in diethyl ether as the solvent with n-butyl lithium or potassium t-butoxide as the base at a temperature of 0° C. warming to room temperature.

Compounds of formula (VIII) may be prepared by the coupling of a compound of formula (IX):

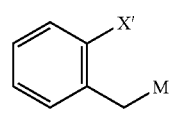

(IX)

wherein X' is Br, I or OTf where OTf is trifluomethanesulphonate and M is MgQ or ZnQ, where Q is Cl, Br or I.
and a compound of formula (X):

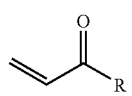

(X)

wherein R represents a methyl or ethyl group.

Preferably the reaction is carried out in a polar solvent such as tetrahydrofuran and diethylether at a temperature in the range of −78° C. to +25° C. If M is a magnesium halide, the reaction is preferably carried out in the presence of a copper (I) salt. In one embodiment, the reaction is preferably carried out with a magnesium bromide reagent in diethylether at −78° C. in the presence of a CuBr.Me$_2$S complex. The reaction is particularly suitable for use with compounds of formula (IX) in which X' is bromine atom.

If M is a zinc halide, the reaction is preferably carried out in the presence of a complex of LiCl and CuCN. In one embodiment, the reaction is preferably carried out using a compound of formula (IX) in which M is ZnQ where Q represents Br in the presence of a 2:1 LiCl:CuCN complex as well as one equivalent of TMSCI in THF at −78° C. The reaction is particularly suitable for use with compounds of formula (IX) in which X' is a bromine or an iodine atom.

Preferably X' is I and ZnQ is ZnBr.

Compounds of formula (IX) are either commercially available or may be prepared by standard methodology.

The vinyl ketones (X) where R represents a methyl or ethyl group are commercially available.

The trifluoromethyl ketone intermediate of formula (IV) may alternatively be prepared from a compound of formula (XI):

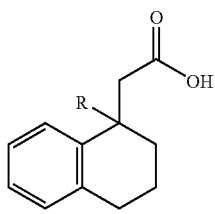

(XI)

wherein R represents a methyl or ethyl group.

In one variant, a compound of formula (XI) may be converted to the corresponding acid chloride by treatment with oxalyl chloride or thionyl chloride in the presence of a catalytic amount of N,N-dimethyl formamide in an inert solvent such as toluene or dichloromethane at a non-extreme temperature between 0 to 110° C. Oxalyl chloride in toluene with a catalytic amount of dimethyl formamide at room temperature is preferred. The crude acid chloride may then be treated with an organic base such as pyridine and a trifluoroacetylating reagent such as trifluoroacetic anhydride in an inert solvent such as dichloromethane at a non-extreme temerature of 0 to 40° C. to afford the compound of formula (IV). The preferable conditions are pyridine and trifluoroacetic anhydride in dichloromethane at room temperature.

In a second variant, compounds of formula (IV) may be prepared in a two stage process by conversion of compounds of formula (XI) into its corresponding ester followed by conversion of the ester into (IV). There are many processes for the conversion of an acid into its ester including those described in "Comprehensive Organic Transformations" R. C. Larock, VCH, 1989, pp 966-972. Preferably, the methyl ester is used and is prepared by treatment of a compound of formula (XI) with methyl iodide and anhydrous potassium carbonate in acetone at room temperature. In the second stage, the ester is converted into a compound of formula (IV) by treatment with a solution of trifluoromethane in the presence of strong base in dry dimethyl formamide at −30 to +10° C. Preferably, the strong base is potassium bis(trimethylsilyl) amide and the temperature is −10° C.

The second variant, the two stage process for the preparation of a compound of formula (IV) from a compound of formula (XI), is preferred.

Compounds of formula (XI) may be prepared from compounds of formula (XII):

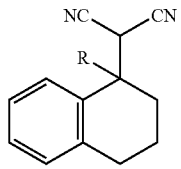

(XII)

wherein R represents a methyl or ethyl group.

There are many processes for the hydrolysis of nitrites to carboxylic acids including those described in "Comprehensive Organic Transformations" R. C. Larock, VCH, 1989, p 993. The hydrolysis may be carried out in the presence of an inorganic base in solvent(s) including alcohols and water at a non-extreme temperature from 50 to 200° C. Preferably the hydrolysis is performed using potassium hydroxide as base in a water/ethylene glycol mixture at reflux. Decarboxylation of the resultant product can be achieved thermally by heating in the presence or absence of a high boiling solvent at a non-extreme temperature of 100 to 200° C. Heating in diethyl glycol at 130° C. is preferred.

Compounds of formula (XII) may be prepared from a compound of formula (XIII):

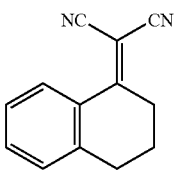

(XIII)

Conjugate addition of nucleophiles to the compound of formula (XIII) may be achieved by many methods including those detailed in "Organometallics in Synthesis" M. Schlosser (editor), Wiley 1994 pp 283-376. Preferably, the Grignard reagent is added to copper(I) iodide in an inert solvent such as diethyl ether or tetrahydrofuran and then compound (VIII) added at a non extreme temperature of −20 to 65° C. Preferably tetrahydrofuran is the solvent and the reaction is performed at 0° C. until all the reagents are combined and then at reflux.

The compound of formula (XIII), 3,4-dihydro-1(2H)-naphthalenylidenepropanedinitrile, may be prepared from commercially available α-tetralone as described in the literature (see, for example, Russian Chemical Bulletin (Translation of Izvestiya Akademii Nauk, Seriya Khimicheskaya) 2003 52(10): 2235-2240).

A second process (B) according to the invention for the preparation of compounds of formula (I) comprises reduction of a Schiff's base of formula (XIV):

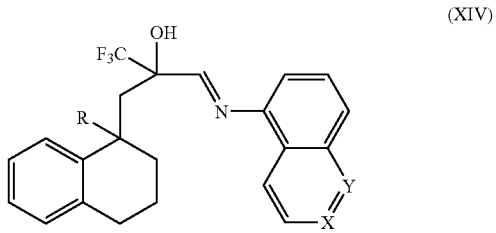

(XIV)

wherein the groups R, X and Y are as defined above for compounds of formula (I)

Reduction may be achieved by treatment with a variety of reducing agents such as sodium cyanoborohydride or sodium triacetoxyborohydride in a suitable solvent, for example, acetic acid.

Compounds of formula (XIV) may be prepared by reaction of an aldehyde of formula (XV)

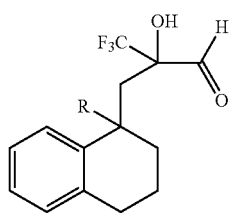

(XV)

wherein R represents a methyl or ethyl group
with a quinolinamine or isoquinolinamine of formula (III).

This reaction may be effected in a suitable solvent, such as acetic acid and may be facilitated by conducting the reaction in a microwave reactor. The Schiff's base (XIV) may be isolated from this reaction but may also be reduced in situ to give compound of formula (I) directly.

Compounds of formula (XV) may be obtained by oxidation of compounds of formula (XVI)

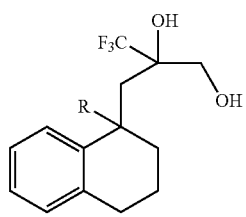

(XVI)

wherein R represents a methyl or ethyl group.

Oxidation may be achieved using, for example, pyridine sulphur trioxide complex in DMSO in the presence of triethylamine.

Compounds of formula (XVI) may be prepared by dihydroxylation of compounds of formula (V) for example using potassium permanganate, osmium tetroxide or asymmetric dihydroxylation reagents such as AD-mix α and β as described by Sharpless in J Org Chem, 1992, 2768-2771.

Certain compounds of formula (II), (IV), (V), (VI), (VII), (VIII), (XI) when R represents ethyl, (XII), (XIV), (XV) and (XVI) are new and form an aspect of the invention.

In addition processes for preparing formulations including one or more compounds of formula (I) form an aspect of this invention.

Compositions comprising a compound of the invention also constitute an aspect of the invention.

Compounds of the invention may be expected to demonstrate good anti-inflammatory properties. They also may be expected to have an attractive side-effect profile, demonstrated, for example, by increased selectivity for glucocorticoid receptor mediated transrepression over transactivation and are expected to be compatible with a convenient regime of treatment in human patients.

The invention will now be illustrated by way of the following non-limiting examples.

EXAMPLES

Synthetic Experimental

Abbreviations
THF Tetrahydrofuran
DCM Dichloromethane
DMA N,N-dimethylacetamide
DMF N,N-dimethylformamide
DMSO Dimethyl sulphoxide
EtOH Ethanol
HCl Hydrochloric acid
TLC Thin layer chromatography
TMSCF$_3$ Trimethyl(trifluoromethyl)silane
NH$_4$Cl Ammonium chloride
HPLC High performance liquid chromatography
MeCN Acetonitrile
CDCl$_3$ Deuterochloroform
SPE Solid phase extraction
EtOAc Ethyl acetate
NH$_4$Cl Ammonium chloride
RT Room temperature
General Experimental Conditions
LCMS LCMS spectra were recorded on an Hewlett-Packard 1050 or 1100 LC system and a Waters ZQ mass spectrometer with ES$^+$ and ES$^-$ ionisation, a 3 μm ABZ+PLUS 3.3 cm×4.6 mm ID column was used at a flow rate of 3 ml/min and injection volume of 5 μl with the following gradient.

Solvent A: 0.1% Formic Acid+10 mMolar Ammonium Acetate:
Solvent B: 95% Acetonitrile+0.05% Formic Acid

| Gradient: | | |
|---|---|---|
| Time | A % | B % |
| 0.00 | 100 | 0 |
| 0.70 | 100 | 0 |
| 4.20 | 0 | 100 |
| 5.30 | 0 | 100 |
| 5.50 | 100 | 0 |

Detection by UV was in the range 215 to 330 nm using Sedere Sedex 55 at 40° C. and a nitrogen gas flow at 2.2 bar.
LCUV LCUV analysis was performed using an Hewlett-Packard 1050 with a 30 min gradient, a 3 μm ABZ+PLUS column with dimensions 3.3 cm×4.6 mm ID was used with a 1 ml/min flow rate and injection volume of 5 μl, with the following gradient:

Solvent A: 0.1% Formic Acid+10 mMolar Ammonium Acetate:
Solvent B: 95% Acetonitrile+0.05% Formic Acid

| Gradient: | | |
|---|---|---|
| Time | A % | B % |
| 0.00 | 100 | 0 |
| 2.00 | 100 | 0 |
| 22.0 | 0 | 100 |
| 27.0 | 0 | 100 |
| 29.0 | 100 | 0 |
| 30.0 | 100 | 0 |

Mass Directed Autopreparative HPLC

Autopreparative HPLC was carried out using a Waters 600 gradient pump, Waters 2767 inject/collector, Waters Reagent Manager, Micromass ZMD mass spectrometer, Gilson Aspec waste collector and Gilson 115 post-fraction UV detector. The column used was typically a Supelco LCABZ++ column with dimension of 20 mm internal diameter by 100 mm in length. The stationary phase particle size is 5 µm. The flow rate was 20 ml/min and the runtime was 15 minutes, which comprises a 10-minute gradient followed by a 5 minute column flush and re-equilibration step.

Solvent A: Aqueous solvent=water+0.1% formic acid
Solvent B: Organic solvent=MeCN: water 95:5+0.05% formic acid Specific gradients used were dependent upon the retention time in the analytical system. For 2.0-2.8 min, 5-30% B, 2.5-3.0 min, 15-55% B, 2.8-4.0 min, 30-80% B and 3.8-5.5 min, 50-90% B.

NMR $^1$H NMR spectra were recorded in either $CDCl_3$ or DMSO-$d_6$ on either a Bruker DPX 400 or Bruker Avance DRX spectrometer both working at 400 MHz and 9.4 Tesla using as an internal standard either tetramethylsilane or the residual protonated solvent. For $CDCl_3$ and DMSO-$d_6$ this was referenced to 7.25 and 2.50 ppm respectively. $^{19}$F NMR spectra were recorded in either $CDCl_3$ or DMSO-$d_6$ using the same instrumentation and are referenced to TFA at −76 ppm.

Microwave

Microwave reactions were conducted using a Smith Creator 300 watt monomode microwave reactor.

Experimental

Intermediate 1

5-(2-Iodophenyl)pentan-2-one

A suspension of dry lithium chloride (6.4 g, 150 mmol) and cuprous cyanide (6.72 g, 75 mmol) in anhydrous tetrahydrofuran (75 ml) was stirred under nitrogen for 15 min at 21° C. and then cooled to −73°. A 0.5M solution of 2-iodobenzylzinc bromide in tetrahydrofuran (150 ml, 75 mmol) was added dropwise over 40 min below −65° C. and the temperature was allowed to rise to −7° C., stirred at this temperature for 0.5 h and then cooled back to −68° C. Chlorotrimethylsilane (19 ml, 150 mmol) was added over 10 min and stirring continued for a further 15 min. A solution of methylvinylketone (6.25 ml, 75 mmol) in anhydrous tetrahydrofuran (150 ml) was dried over anhydrous sodium sulphate and then added to the reaction over 25 min. The mixture was stirred in an acetone/cardice bath for 19 h, reaching −30° C., and then without cooling for 3 h. Aqueous ammonium chloride solution (200 ml) was added carefully and the reaction mixture was extracted with ether (2×200 ml). The combined organic layers were washed with water (200 ml) (a white solid was filtered off and discarded) and saturated brine (200 ml), dried over anhydrous magnesium sulphate and evaporated. The resulting oil was dissolved in cyclohexane (200 ml), solid was filtered off, and the filtrate was evaporated to give an oil (17.6 g). A 2 g portion was purified by flash chromatography on a 90 g Biotage cartridge eluting with an 8:1 mixture of cyclohexane and toluene to give the title compound as a liquid (1.112 g).

LCMS: retention time 3.20 min, $MNH_4^+$ 306

The remaining crude product was purified on an 800 g Biotage cartridge eluting with a 9:1 mixture of cyclohexane and t-butyl methyl ether to give a further 8.25 g of product, total yield 9.36 g, 43%

Intermediate 2

1-Iodo-2-(4-methylpent-4-en-1-yl)benzene

To a stirred solution of potassium t-butoxide (7.96 g, 71 mmol) in anhydrous ether (100 ml) under nitrogen, was added methyltriphenylphosphonium bromide (25.6 g, 71 mmol). The yellow mixture was stirred under reflux for 0.5 h, allowed to cool for 10 min, and then a solution of 5-(2-iodophenyl)pentan-2-one (Intermediate 1) (9.3 g, 32.3 mmol) in anhydrous ether (70 ml) was added over 20 min. The reaction mixture was refluxed for 1 h, allowed to cool and then poured onto ice. Ether (100 ml) and water (100 ml) were added and the layers were separated. The aqueous layer was re-extracted with ether (100 ml) and the combined organic layers were washed successively with water (100 ml) and saturated brine (100 ml), dried over anhydrous magnesium sulphate and evaporated to dryness. The residue was treated with heptane (200 ml), solid was filtered off and washed with heptane and the filtrate was evaporated. The oil obtained was purified on a 90 g silica cartridge eluted with heptane to give the title compound as a liquid (8.34 g, 90%).

LCMS: retention time 3.97 min $^1$H—NMR ($CDCl_3$) 1.79 (2H, m), 1.81 (3H, s), 2.16 (2H, t), 2.75 (2H, t), 4.79 (2H, d), 6.93 (1H, t), 7.25-7.35 (3H, m)

Intermediate 3

Tributyl[1-(trifluoromethyl)ethenyl]stannane

A 2M solution of LDA in tetrahydrofuran (7.5 ml, 15 mmole) was added to tetrahydrofuran (5 ml) at −5° C. To this solution was added tri-n-butylstannane (4.36 g, 15 mmole) dropwise and the mixture was left to stir for 20 min. In a second flask, copper(I)iodide (1.43 g, 7.5 mmoles) was suspended in tetrahydrofuran (5 ml). The flask was cooled to −10° C. and the lithium tri-n-butylstannane solution was then transferred dropwise via a syringe to the copper(I)iodide suspension. The mixture was stirred at −10° C. for 0.5 h, cooled to −78° C. then treated dropwise with 2-bromotrifluoropropene (1.32 g, 7.5 mmole). Stirring was continued for a further 0.5 h followed by 1 h at room temperature. Volatiles were removed in vacuo and the residue was dissolved in ether (100 ml), filtered and the solvent was removed to give an oil. Purification was by distillation. The fraction boiling at 114° C./4.6 mbar was collected to give the title compound (2.16 g, 75%).

$^1$H—NMR: ($CDCl_3$) 6.42 (s, 1H), 5.68 (s, 1H), 1.50 (m, 6H), 1.32 (m, 6H). 1.03 (m, 6H), 0.91 (t, 9H)

Intermediate 4

1-Methyl-1-[2-(trifluoromethyl)prop-2-en-1-yl]-1,2,3,4-tetrahydronaphthalene

To a solution of 1-iodo-2-(4-methylpent-4-en-1-yl)benzene (Intermediate 2) (8.3 g, 29 mmol), triphenylphosphine (1.57 g, 6 mmol), cuprous iodide (0.572 g, 3 mmol) and palladium acetate (0.673 g, 3 mmol) in anhydrous N,N-dimethylformamide (200 ml) was added tributyl[1-(trifluoromethyl)ethenyl]stannane (Intermediate 3) (14.5 g, 37.7 mmol). The flask was evacuated and filled with nitrogen four times and then placed in a bath preheated to 110° C. and stirred for 3 h. The mixture was allowed to cool, the solution was decanted from the black solid and concentrated to low volume. Heptane (200 ml) and water (200 ml) were added, insoluble material was filtered off, and the layers were separated. The aqueous layer was re-extracted with heptane (100 ml) and the combined organic layers were washed successively with water (2×200 ml), aqueous lithium chloride solution (200 ml), water (200 ml) and saturated brine (200 ml), dried over anhydrous sodium sulphate and evaporated. The resulting oil was purified by flash chromatography on an 800 g Biotage silica cartridge eluted with heptane to give the title compound (5.28 g, 72%).

LCMS: retention time 3.89 min $^1$H—NMR: (CDCl$_3$) 1.44 (3H, s), 2.54 & 2.89 (2H, Abq), 2.87(2H, d), 5.02 (1H, s), 5.76 (1H, s), 7.15-7.32 (3H, m), 7.41 (1H, d)

$^{19}$F—NMR: (CDCl$_3$) −68.5

Intermediate 5

3,3,3-Trifluoro-2-[(1-methyl-1,2,3,4-tetrahydro-1-naphthalenyl)methyl]-1.2-propanediol To a solution of 1-methyl-1-[2-(trifluoromethyl)prop-2-en-1-yl]-1,2,3,4-tetrahydronaphthalene (Intermediate 4) (2.03 g, 8 mmol) in t-butanol (50 ml) and water (50 ml) were added AD-mix α (30 g) and AD-mix β (30 g). The suspension was stirred at 40° C. under nitrogen for 19 h. Further AD-mix α (10 g), AD-mix β (10 g), t-butanol (20 ml) and water (20 ml) were added and stirring continued for 22 h. The solid was filtered off and washed with ether (3×50 ml), more ether (200 ml) was added to the filtrate, which was then carefully added to aqueous sodium metabisulphite solution (300 ml) and stirred for 10 min, when effervescence had ceased. The layers were separated and the aqueous layer was re-extracted with ether (200 ml). The combined organic layers were washed successively with ca 125 ml portions of water, 2M hydrochloric acid, water, saturated sodium bicarbonate solution, water and saturated brine, dried over anhydrous sodium sulphate and evaporated to give an oil. The crude product was purified by flash chromatography on a 90 g Biotage cartridge eluting with 15% ethyl acetate in cyclohexane to give the title compound (1.60 g, 70%).

LCMS: retention time 3.20 min, MNH$_4^+$ 306, M-H$^-$ 287

$^{19}$F—NMR: (CDCl$_3$) −80.6, −81.2 (43:57 ratio of diastereomers)

Intermediate 6

3,3,3-Trifluoro-2-hydroxy-2-[(1-methyl-1,2,3,4-tetrahydro-1-naphthalenyl)methyl]propanal To a solution of 3,3,3-trifluoro-2-[(1-methyl-1,2,3,4-tetrahydro-1-naphthalenyl)methyl]-1,2-propanediol (Intermediate 5) (1.6 g, 5.55 mmol) in anhydrous dichloromethane (36 ml), anhydrous dimethylsulphoxide (12 ml) and triethylamine (4.9 ml, 35 mmol) stirred under nitrogen in a bath at 8.5° C., was added pyridine-sulphur trioxide complex (4.45 g, 28 mmol) portionwise over 20 min. The solution was stirred in the ice-water bath for a further 1.5 h and then allowed to warm to 21° C. and stirred for 17 h. The reaction mixture was added to aqueous ammonium chloride solution (100 ml) and dichloromethane (100 ml) and the layers were separated. The aqueous layer was re-extracted with dichloromethane (100 ml) and the combined organic layers were washed successively with water (6×100 ml) and saturated brine (100 ml), dried over anhydrous magnesium sulphate and evaporated. The yellow oil obtained was purified by flash chromatography on a 90 g Biotage cartridge eluting with 5% ether in cyclohexane to give the title compound as an oil (1.24 g, 78%).

LCMS: retention time 3.49 and 3.52 min, MNH$_4^+$ 304 (44:56 ratio of diastereomers)

$^{19}$F—NMR: (CDCl$_3$) −78.03, −78.19 (40:60 ratio of diastereomers)

Intermediate 7

1,1,1-Trifluoro-3-(1-methyl-1,2,3,4-tetrahydro-1-naphthalenyl)-2-[(5-guinolinylimino) methyl]-2-propanol A solution of 3,3,3-trifluoro-2-hydroxy-2-[(1-methyl-1,2,3,4-tetrahydro-1-naphthalenyl)methyl]propanal (Intermediate 6) (200 mg, 0.7 mmol) and 5-quinolinamine (131 mg, 0.9 mmol) in glacial acetic acid (4 ml) was microwaved at 160° C. for 30 min. The solution was added to toluene (25 ml) and evaporated and the remaining acetic acid was azeotroped by evaporating again with toluene (50 ml). The crude product was purified on a 5 g silica Bond Elut cartridge eluting with 1:1 cyclohexane:dichloromethane followed by a 10:1 to 3:1 gradient of cyclohexane:ethyl acetate to give the title compound (177 mg, 60%).

LCMS: retention time 3.77 and 3.81 min, MH$^+$ 413 (38:62 ratio of diastereomers)

$^{19}$F—NMR: (CDCl$_3$) −79.78, −79.99 (57:43 ratio of diastereomers)

Intermediate 8

1,1,1-Trifluoro-3-[(2-methyl-5-guinolinyl)imino]-2-[(1-methyl-1,2,3,4-tetrahydro-1-naphthalenyl)methyl]-2-propanol Intermediate 8 was prepared from 3,3,3-trifluoro-2-hydroxy-2-[(1-methyl-1,2,3,4-tetrahydro-1-naphthalenyl)methyl]propanal (Intermediate 6) and 2-methyl-5-quinolinamine using a similar method to that described for Intermediate 7.

LCMS: retention time 3.64 and 3.73 min, MH$^+$ 427 (48:52 ratio of diastereomers)

$^{19}$F—NMR: (CDCl$_3$) −79.80, −80.02 (54:46 ratio of diastereomers)

Intermediate 9

1,1,1-Trifluoro-3-(5-isoguinolinylimino)-2-[(1-methyl-1,2,3,4-tetrahydro-1-naphthalenyl) methyl]-2-propanol Intermediate 9 was prepared from 3,3,3-trifluoro-2-hydroxy-2-[(1-methyl-1,2,3,4-tetrahydro-1-naphthalenyl)methyl]propanal (Intermediate 6) and 5-isoquinolinamine using a similar method to that described for Intermediate 7.

LCMS: retention time 3.69 and 3.74 min, MH$^+$ 413 (40:60 ratio of diastereomers)

$^{19}$F—NMR: (CDCl3) −79.7, −79.97 (56:44 ratio of diastereomers)

Intermediate 10

6-(2-Iodophenyl)-3-hexanone

Lithium chloride (6.6 g, 150 mmole) (dried overnight at 115° C. under vacuum) and copper(I) cyanide (6.72 g, 75 mmole) were stirred with tetrahydrofuran (75 ml) under nitrogen for 10 minutes then cooled to −78° C. A solution of 2-iodobenzyl zinc bromide (150 ml, 0.5M in THF, 75 mmol) was added and the mixture was warmed to −15° C., held at this temperature for 20 min then re-cooled to −78° C. Chlorotrimethylsilane (19.1 ml, 150 mmol) was added followed by a solution of ethyl vinyl ketone (7.4 ml, 74.3 mmol) in tetrahydrofuran (15 ml). The mixture was stirred at −78° C. for 3 hours then warmed to room temperature and stirred for 1 hour before being poured into a mixture of water (400 ml) and ether (400 ml). The aqueous layer was extracted with ether (2×400 ml) and the combined ethereal solutions were washed with brine (2×200 ml), dried over anhydrous magnesium sulphate and evaporated in vacuo to give the title compound as a pale yellow liquid (23 g).

$^1$H—NMR: (CDCl$_3$) 7.81 (d, 1H), 7.30-7.18 (m, 2H), 6.88 (m, 1H), 2.72 (t, 2H), 2.48 (m, 4H), 1.80 (m, 2H), 1.07 (t, 3H)

Intermediate 11

1-(4-Ethyl-4-penten-1-yl)-2-iodobenzene

A suspension of methyltriphenylphosphonium bromide (21.76 g, 61 mmol) in dry ether (300 ml) was stirred at 0° C. under nitrogen. To this was added a 1.6M solution of butyl lithium (33.3 ml, 53.3 mmole) dropwise. Stirring at 0° C. was continued for 45 min then a solution of 6-(2-iodophenyl)-3-hexanone (Intermediate 10) (11.5 g, 38 mmol) in dry ether (40 ml) was added dropwise. Stirring at 0° C. was continued for 3 hours after which time aqueous ammonium chloride solution was added and the mixture was extracted with ether. The combined extracts were washed once with a mixture of ammonium chloride and sodium chloride solutions, dried over anhydrous magnesium sulphate and evaporated in vacuo. The residue was slurried with cyclohexane to extract the crude product. Purification by SPE eluting with cyclohexane gave the title compound as a colourless liquid (6.8 g, 60%).

LCMS: retention time 4.19 min, no significant ions
$^1$H—NMR: (CDCl$_3$) 7.82 (d, 1H), 7.30-7.20 (m, 2H), 6.88 (m, 1H), 4.75 (s, 2H), 2.72 (t, 2H), 2.18-2.02 (m, 4H), 1.75 (m, 2H), 1.05 (t, 3H)

Intermediate 12

1-Ethyl-1-[2-(trifluoromethyl)-2-propen-1-yl]-1,2,3,4-tetrahydronaphthalene 1-(4-Ethyl-4-penten-1-yl)-2-iodobenzene (Intermediate 11) (1.1 g, 3.66 mmole), tributyl[1-(trifluoromethyl)ethenyl]stannane (Intermediate 3) (1.4 g, 3.64 mmole), triphenyl phosphine (188 mg, 0.717 mmole), palladium acetate (82 mg, 0.365 mmole) and copper(I) iodide (69 mg, 0.362 mmole) were dissolved in dry DMF (60 ml). The solution was degassed by evacuating and filling the flask with nitrogen four times. The solution was then immediately immersed in a 110° C. oil bath, left to react for 3.5 h, cooled to room temperature then partitioned between water (100 ml) and cyclohexane (100 ml). The layers were separated and the aqueous layer was extracted with further cyclohexane (100 ml). The combined extracts were dried over anhydrous sodium sulphate and evaporated and the residue was applied to a silica Solid Phase Extraction (SPE) cartridge. Elution with cyclohexane gave the title compound (1.36 g) containing some residual impurities. This was used without additional purification.

Intermediate 13

3-(1-Ethyl-1,2,3,4-tetrahydro-1-naphthalenyl)-1,1,1-trifluoro-2-propanone

1-Ethyl-1-[2-(trifluoromethyl)-2-propen-1-yl]-1,2,3,4-tetrahydronaphthalene (Intermediate 12) (120 mg, 0.447 mmole) was dissolved in methanol (25 ml) and cooled to −78° C. Ozone was bubbled through the solution for 5 min followed by oxygen for 10 min then nitrogen for 10 min. Dimethyl sulphide (4 ml, 54 mmole) was added and the dry-ice bath was removed to bring the mixture to room temperature. Stirring was continued for 30 min then volatiles were removed in vacuo. The residue was purified on a 10 g silica SPE cartridge eluting with cyclohexane (200 ml), cyclohexane:ethyl acetate 80:20 (100 ml) and ethyl acetate (100 ml) to give the title compound (31 mg, 26%).

$^1$H—NMR: (CDCl$_3$) 7.10 (m, 4H), 3.20 (d, 1H), 3.0 (d, 1H), 2.95-2.75 (m, 2H), 2.06-1.75 (m, 6H), 0.82 (t, 3H)

Intermediate 14 (Racemic Diastereomer 1)
Intermediate 15 (Racemic Diastereomer 2)

2-[(1-Ethyl-1,2,3,4-tetrahydro-1-naphthalenyl)methyl]-2-(trifluoromethyl)oxirane (D1)

2-[(1-Ethyl-1,2,3,4-tetrahydro-1-naphthalenyl)methyl]-2-(trifluoromethyl)oxirane (D2)

To a suspension of sodium hydride (74 mg of a 60% dispersion in mineral oil, 1.85 mmol) in DMSO (5 ml) was added a solution of trimethylsulphoxonium iodide (610 mg, 2.77 mmol) in DMSO (5 ml). After stirring at room temperature for 30 min a solution of 3-(1-ethyl-1,2,3,4-tetrahydro-1-naphthalenyl)-1,1,1-trifluoro-2-propanone (Intermediate 13) (500 mg, 1.85 mmol) in THF (3 ml) was added and the mixture was stirred at room temperature for 2 h. The reaction mixture was poured into water and extracted with diethylether. The organic extract was washed repeatedly with water, dried over anhydrous sodium sulphate and evaporated in vacuo to give the title compound as a crude mixture of diastereomers. Extraction of aqueous layer with dichloromethane yielded further title compound as a crude mixture of diastereomers. Combined products were then applied to a 20 g silica SPE cartridge eluting with a 0-10% dichloromethane in cyclohexane gradient for 10 min followed by 10% dichloromethane in cyclohexane for 5 min. This gave, in order of elution, Intermediate 14 (racemic diastereomer 1, 178 mg): and Intermediate 15 (racemic diastereomer 2, 86 mg).

Intermediate 14 (Racemic Diastereomer 1)
$^1$H—NMR: (CDCl$_3$) 7.19-7.05 (m, 4H), 2.75 (m, 2H), 2.67 (d, 1H), 2.59 (d, 1H), 2.24-2.18 (m, 2H), 1.88-1.72 (m, 5H), 1.64-1.55 (m, 1H), 0.84 (t, 3H)

Intermediate 15 (Racemic Diastereomer 2)
$^1$H—NMR: (CDCl$_3$) 7.19-7.03 (m, 4H), 2.79-2.74 (m, 3H), 2.53 (d, 1H), 2.33 (m, 1H), 2.27 (d, 1H), 1.87-1.55 (m, 6H), 0.80 (t, 3H)

Intermediate 16

2-[(1-Ethyl-1,2,3,4-tetrahydro-1-naphthalenyl)methyl]-3,3,3-trifluoro-1,2-propanediol 1-Ethyl-1-[2-(trifluoromethyl)-2-propen-1-yl]-1,2,3,4-tetrahydronaphthalene (Intermediate 12) (100 mg, 0.373 mmole), AD-MIX-α (300 mg) and AD-MIX-β (300 mg) in t-butanol (2 ml) and water (2 ml) were stirred at room temperature. After 1 hour further AD-MIX-α (600 mg) and AD-MIX-β (600 mg) were added and the mixture was heated to 30° C. for 18 h. Sodium sulphite (2 g) was added together with water (5 ml) then stirred for 10 min. Extraction of the mixture with ethyl acetate (3×20 ml) followed by washing of the extract with 2M HCl (x2), 2M NaOH and evaporation of volatiles in vacuo gave a crude product. After purification (silica SPE, 85:15 cyclohexane:ethyl acetate) the title compound was obtained (30 mg, 27%).

LCMS: retention time 3.39 min, MNH$_4^+$ 320

Intermediate 17

2-[(1-Ethyl-1,2,3,4-tetrahydro-1-naphthalenyl)methyl]-3,3,3-trifluoro-2-hydroxypropanal To a solution of 2-[(1-ethyl-1,2,3,4-tetrahydro-1-naphthalenyl)methyl]-3,3,3-trifluoro-1,2-propanediol (Intermediate 16) (2.03 g, 6.71 mmol) in anhydrous dichloromethane (50 ml), anhydrous dimethylsulphoxide (50 ml) and triethylamine (5.9 ml, 42 mmol) stirred under nitrogen in an ice-water bath at 9° C., was added pyridine-sulphur trioxide complex (5.37 g, 33 mmol) portionwise over 20 min. The solution was then allowed to warm to room temperature and stirred for 65 h. The reaction mixture was added to aqueous ammonium chloride solution (350 ml) and extracted into dichloromethane (×2). The combined organic layers were washed successively with water (2×200 ml) and saturated brine (2×200 ml), dried over anhydrous magnesium sulphate and evaporated in vacuo. The brown oil obtained was applied to a 50 g silica SPE cartridge eluting with 0 to 100% dichloromethane in heptane gradient to give the title compound as a mixture of diastereomers (380 mg, 19%).

LCMS: retention time 3.64 min, M+NH$_4^+$ 318
$^{19}$F—NMR: (CDCl$_3$) −77.9 and −78.3 (40:60 ratio of diastereomers)

Intermediate 18

3-(1-Ethyl-1,2,3,4-tetrahydro-1-naphthalenyl)-1,1,1-trifluoro-2-[(5-isoguinolinylimino) methyl]-2-propanol A solution of 2-[(1-ethyl-1,2,3,4-tetrahydro-1-naphthalenyl)methyl]-3,3,3-trifluoro-2-hydroxypropanal (Intermediate 17) (220 mg, 0.73 mmol) and 5-isoquinolinamine (144 mg, 1.0 mmol) in glacial acetic acid (4 ml) was microwaved at 150° C. for 20 min. The solution was added to toluene and evaporated in vacuo to yield an orange residue. The crude product was purified on a 10 g silica SPE cartridge eluting with 0 to 100% dichloromethane in heptane gradient to give the title compound as a mixture of diastereomers (190 mg, 61%).

LCMS: retention time 3.74 min, MH$^+$ 427
$^{19}$F—NMR: (CDCl$_3$) −79.82 and −79.88

Example 1

1,1,1-Trifluoro-3-(1-methyl-1,2,3,4-tetrahydro-1-naphthalenyl)-2-[(5-guinolinylamino) methyl]-2-propanol To a solution of 1,1,1-trifluoro-3-(1-methyl-1,2,3,4-tetrahydro-1-naphthalenyl)-2-[(5-quinolinylimino) methyl]-2-propanol (Intermediate 7) (172 mg, 0.417 mmol) in glacial acetic acid (4 ml) stirred under nitrogen at 21° C., was added sodium triacetoxyborohydride (353 mg, 1.66 mmol) portionwise over 25 min and the solution was stirred for a further 4 h. The solution was then carefully added to a mixture of saturated aqueous sodium carbonate (50 ml) and ethyl acetate (30 ml) and stirred for 10 min, when effervescence had finished. The layers were separated and the aqueous layer re-extracted with ethyl acetate (30 ml) and the combined organic layers were washed with saturated sodium carbonate (15 ml), water (2×30 ml) and saturated brine (30 ml), dried over anhydrous sodium sulphate and evaporated. The crude product was purified on a 50 g silica cartridge using a Flashmaster 2 system with a 0-100% gradient of ethyl acetate in cyclohexane over 40 min to give the title compound (74.3 mg, 43%) as a mixture of diastereomers.

Further purification using mass-directed autopreparative reverse phase HPLC gave Example 1-D1 (racemic diastereomer 1) (10 mg) and Example 1-D2 (racemic diastereomer 2) (8.9 mg).

Example 1-D1(Racemic Diastereomer 1)

LCMS: retention time 3.35 min, MH$^+$ 415
$^{19}$F—NMR: (DMSO-d$_6$) −78.16

Example 1-D2 (Racemic Diastereomer 2)

LCMS: retention time 3.42 min, MH$^+$ 415
$^{19}$F—NMR: (DMSO-d$_6$) −78.05.

Example 1-D1 (racemic diastereomer 1) was separated into its enantiomers using a 2×25 cm Chiralpak AD column eluting with 60% ethanol in heptane with a flow rate of 15 m/min to yield Example 1-D1E1 (enantiomer 1 of diastereomer 1) eluting around 3.8 min and Example 1-D1E2 (enantiomer 2 of diastereomer 1) around 6.8 min.

Example 1-D1E1 (Enantiomer 1 of Diastereomer 1)

Analytical chiral HPLC (25×0.46 cm Chiralpak AD column, 60% ethanol in heptane eluting at 1 ml/min): retention time 3.14 min.
LCMS: MH$^+$ 415
$^{19}$F—NMR: (CDCl$_3$) −80.31

Example 1-D1E2 (Enantiomer 2 of Diastereomer 1)

Analytical chiral HPLC (25×0.46 cm Chiralpak AD column, 60% ethanol in heptane eluting at 1 ml/min): retention time 5.68 min.
LCMS: MH$^+$ 415
$^{19}$F—NMR: (CDCl$_3$) −80.32

Example 2

1,1,1-Trifluoro-3-[(2-methyl-5-quinolinyl)amino]-2-[(1-methyl-1,2,3,4-tetrahydro-1-naphthalenyl)methyl]-2-propanol To a solution of 1,1,1-trifluoro-3-[(2-methyl-5-quinolinyl)imino]-2-[(1-methyl-1,2,3,4-tetrahydro-1-naphthalenyl)methyl]-2-propanol (intermediate 8) (130 mg, 0.30 mmol) in glacial acetic acid (4 ml) stirred under nitrogen at 21° C., was added sodium triacetoxyborohydride (254 mg, 1.2 mmol) portionwise over 25 min and the solution was stirred for a further 4 h. The solution was then carefully added to a mixture of saturated aqueous sodium carbonate (50 ml) and ethyl acetate (30 ml) and stirred for 10 min, when effervescence had finished. The layers were separated and the aqueous layer re-extracted with ethyl acetate (30 ml) and the combined organic layers were washed with saturated sodium carbonate (15 ml), water (2×30 ml) and saturated brine (30 ml), dried over anhydrous sodium sulphate and evaporated. The crude product was purified on a 50 g silica cartridge using a Flashmaster 2 system with a 0-100% gradient of ethyl acetate in cyclohexane over 80 min to give the title compound (91.6 mg, 71%) as a mixture of diastereomers.

Further purification using mass-directed autopreparative reverse phase HPLC gave Example 2-D1 (racemic diastereomer 1) (7.1 mg) and Example 2-D2 (racemic diastereomer 2) (5.5 mg).

Example 2-D1 (Racemic Diastereomer 1)

LCMS retention time 2.89 min, MH$^+$ 429
$^{19}$F—NMR: (DMSO-d$_6$) −78.16

Example 2-D2 (Racemic Diastereomer 2)

LCMS: retention time 2.92 min, MH$^+$ 429
$^{19}$F—NMR: (DMSO-d$_6$) −78.07

Example 2-D1 (racemic diastereomer 1) was separated into its enantiomers using a 2×25 cm Chiralpak AD column eluting with 40% ethanol in heptane with a flow rate of 15 ml/min to yield Example 2-D1E1 (enantiomer 1 of diastereomer 1) eluting around 3.9 min and Example 2-D1E2 (enantiomer 2 of diastereomer 1) around 7.5 min.

Example 2-D1E1 (Enantiomer 1 of Diastereomer 1)

Analytical chiral HPLC (25×0.46 cm Chiralpak AD column, 40% ethanol in heptane eluting at 1 ml/min): retention time 3.22 min.
LCMS: MH$^+$ 429
$^{19}$F—NMR: (CDCl$_3$) −80.37

Example 2-D1E2 (Enantiomer 2 of Diastereomer 1)

Analytical chiral HPLC (25×0.46 cm Chiralpak AD column, 40% ethanol in heptane eluting at 1 ml/min): retention time 6.40 min.
LCMS: MH$^+$ 429
$^{19}$F—NMR: (CDCl$_3$) −80.16

Example 2-D2 (racemic diastereomer 2) was separated into its enantiomers using a 2×25 cm Chiralpak AD column eluting with 3% ethanol in heptane with a flow rate of 15 ml/min to yield Example 2-D2E1 (enantiomer 1 of diastereomer 2) eluting around 13.3 min and Example 2-D2E2 (enantiomer 2 of diastereomer 2) around 16.7 min.

Example 2-D2E1 (Enantiomer 1 of Diastereomer 2)

Analytical chiral HPLC (25×0.46 cm Chiralpak AD column, 3% ethanol in heptane eluting at 1 ml/min): retention time 11.18 min.
LCMS: MH$^+$ 429
$^{19}$F—NMR: (DMSO-d$_6$) −78.07

Example 2-D2E2 (Enantiomer 2 of Diastereomer 2)

Analytical chiral HPLC (25×0.46 cm Chiralpak AD column, 3% ethanol in heptane eluting at 1 ml/min): retention time 13.89 min.
LCMS: MH$^+$ 429
$^{19}$F—NMR: (DMSO-d$_6$) −78.07

Example 3

1,1,1-Trifluoro-3-(5-isoguinolinylamino)-2-[(1-methyl-1,2,3,4-tetrahydro-1-naphthalenyl) methyl]-2-propanol To a solution of 1,1,1-trifluoro-3-(5-isoquinolinylimino)-2-[(1-methyl-1,2,3,4-tetrahydro-1-naphthalenyl) methyl]-2-propanol (Intermediate 9) (154 mg, 0.373 mmol) in glacial acetic acid (4 ml) stirred under nitrogen at 21° C., was added sodium triacetoxyborohydride (316 mg 1.5 mmol) portionwise over 25 min and the solution was stirred for a further 4 h.
The solution was then carefully added to a mixture of saturated aqueous sodium carbonate (50 ml) and ethyl acetate (30 ml) and stirred for 10 min, when effervescence had ceased. The layers were separated and the aqueous layer re-extracted with ethyl acetate (30 ml) and the combined organic layers were washed with saturated sodium carbonate (15 ml), water (2×30 ml) and saturated brine (30 ml), dried over anhydrous sodium sulphate and evaporated. The crude product was purified on a 50 g silica cartridge using a Flashmaster 2 system with a 0-100% gradient of ethyl acetate in cyclohexane over 80 min to give the title compound (92 mg, 59.5%). Early fractions were evaporated to give a pure sample of Example 3-D2 (racemic diastereomer 2) (24.8 mg) whilst late fractions were evaporated to give Example 3-D1 (racemic diastereomer 1) (8.7 mg)

Example 3-D1 (Racemic Diastereomer 1)

LCMS: retention time 3.48 min, MH$^+$ 415
$^{19}$F—NMR: (DMSO-d6) −78.17

Example 3-D2 (Racemic Diastereomer 2)

LCMS: retention time 3.51 min, MH$^+$ 415
$^{19}$F—NMR: (DMSO-d6) −78.03

Example 3-D1 (racemic diastereomer 1) was separated into its enantiomers using a 2×25 cm Chiralcel OD column eluting with 10% ethanol in heptane with a flow rate of 15 m/min to yield Example 3-D1E1 (enantiomer 1 of diastereomer 1) eluting around 6.9 min and Example 3-D1E2 (enantiomer 2 of diastereomer 1) around 9.4 min.

Example 3-D1E1 (Enantiomer 1 of Diastereomer 1)

Analytical chiral HPLC (25×0.46 cm Chiralcel OD column, 10% ethanol in heptane eluting at 1 ml/min): retention time 5.46 min.
LCMS: MH$^+$ 415
$^{19}$F—NMR: (CDCl$_3$) −80.33

Example 3-D1E2 (Enantiomer 2 of Diastereomer 1)

Analytical chiral HPLC (25×0.46 cm Chiralcel OD column, 10% ethanol in heptane eluting at 1 ml/min): retention time 7.45 min.
LCMS: MH$^+$ 415
$^{19}$F—NMR; (CDCl$_3$) −80.32

Example 3-D2 (racemic diastereomer 2) was separated into its enantiomers using a 2×25 cm Chiralcel OD column eluting with 10% ethanol in heptane with a flow rate of 15 ml/min to yield Example 3-D2E1 (enantiomer 1 of diastereomer 2) eluting around 9.0 min and Example 3-D2E2 (enantiomer 2 of diastereomer 2) around 12.4 min.

Example 3-D2E1 (Enantiomer 1 of Diastereomer 2)

Analytical chiral HPLC (25×0.46 cm Chiralcel OD column, 10% ethanol in heptane eluting at 1 ml/min): retention time 7.69 min.
LCMS: MH$^+$ 415

Example 3-D2E2 (Enantiomer 2 of Diastereomer 2)

Analytical chiral HPLC (25×0.46 cm Chiralcel OD column, 10% ethanol in heptane eluting at 1 m/min): retention time 10.32 min.
LCMS: MH$^+$ 415
$^{19}$F—NMR: (CDCl$_3$) −81.21

Example 4

3-(1-Ethyl-1,2,3,4-tetrahydro-1-naphthalenyl)-1,1,1-trifluoro-2-[(5-isoquinolinylamino) methyl]-2-propanol To a solution of 3-(1-ethyl-1,2,3,4-tetrahydro-1-naphthalenyl)-1,1,1-trifluoro-2-[(5-isoquinolinylimino) methyl]-2-propanol (Intermediate 18) (185 mg, 0.43 mmol) in glacial acetic acid (5 ml) stirred under nitrogen at room temperature, was added sodium triacetoxyborohydride (276 mg, 1.3 mmol) and the solution was stirred for approximately 4 h. Further sodium triacetoxyborohydride (100 mg, 0.47 mmol) was added and the reaction was stirred for 1 h. The solution was then carefully added to saturated aqueous sodium carbonate and when effervescence had ceased was extracted into ethyl acetate (×2). The combined organic layers were washed successively with saturated aqueous sodium carbonate solution, water and finally brine/water (1:1), passed through a hydrophobic frit and evaporated in vacuo to yield a pale yellow oil. The crude product was purified on a 10 g silica SPE cartridge eluting with a 0-100% dichloromethane in heptane gradient followed by 1% methanol in dichloromethane. This gave, in order of elution, Example 4-D2 (racemic diastereomer 2) (45 mg) and Example 4-D1 (racemic diastereomer 1) (35 mg).

Example 4-D1 (Racemic Diastereomer 1)

LCMS: retention time 3.56 min, MH$^+$ 429 LCUV: (30 min run) retention time 14.98 min
$^{19}$F—NMR: (CDCl$_3$) −80.36.

Example 4-D2 (Racemic Diastereomer 2)

LCMS: retention time 3.57 min, MH$^+$ 429 LCUV: (30 min run) retention time 15.03 min
$^{19}$F—NMR: (CDCl$_3$) −81.29

Example 4-D1 (racemic diastereomer 1) was separated into its enantiomers using a 2×25 cm Chiralcel OD column eluting with 10% ethanol in heptane with a flow rate of 15 ml/min to yield Example 4-D1E1 (enantiomer 1 of diastereomer 1) eluting around 6.5 min and Example 4-D1E2 (enantiomer 2 of diastereomer 1) around 8.1 min.

Example 4-D1E1 (Enantiomer 1 of Diastereomer 1)

Analytical chiral HPLC (25×0.46 cm Chiralcel OD column, 10% ethanol in heptane eluting at 1 ml/min): retention time 5.26 min.
LCMS: MH$^+$ 429
$^{19}$F—NMR (CDCl$_3$) −80.36

Example 4-D1E2 (Enantiomer 2 of Diastereomer 1)

Analytical chiral HPLC (25×0.46 cm Chiralcel OD column, 10% ethanol in heptane eluting at 1 m/min): retention time 6.69 min.
LCMS: MH$^+$ 429
$^{19}$F—NMR (CDCl$_3$) −80.37

Example 5

3-(1-Ethyl-1,2,3,4-tetrahydro-1-naphthalenyl)-1,1,1-trifluoro-2-[[(2-methyl-5-quinolinyl) amino]methyl]-2-propanol A solution of 2-[(1-ethyl-1,2,3,4-tetrahydro-1-naphthalenyl)methyl]-2-(trifluoromethyl)oxirane (D1, racemic diastereomer 1) (Intermediate 14) (83 mg, 0.29 mmol) in dry dimethylacetamide (1 ml) was added to a mixture of 2-methyl-5-quinolinamine (55 mg, 0.35 mmol) and potassium t-butoxide (39 mg, 0.35 mmol) in dry dimethylacetamide (1 ml) under a nitrogen atmosphere. The reaction was stirred at room temperature for 2 h.

The mixture was then poured into brine/water (1:1) and extracted with ethyl acetate. The organic extracts were washed with further brine/water (1:1), passed through a hydrophobic frit and evaporated in vacuo to yield a brown oil. The crude product was applied first to a 5 g silica SPE cartridge eluting with 0 to 15% ethyl acetate in cyclohexane gradient and then to a 2 g silica SPE cartridge eluting with 0 to 15% diethylether in cyclohexane gradient to give Example 5-D1 (racemic diastereomer 1) (8 mg).

Similar reaction of 2-[(1-ethyl-1,2,3,4-tetrahydro-1-naphthalenyl)methyl]-2-(trifluoromethyl)oxirane (D2, racemic diastereomer 2) (Intermediate 15) with 2-methyl-5-quinolinamine afforded Example 5-D2 (racemic diastereomer 2).

Example 5-D1 (Racemic Diastereomer 1)

LCMS: retention time 3.07 min, MH$^+$ 443

Example 5-D2 (Racemic Diastereomer 2)

LCMS: retention time 3.11 min, MH$^+$ 443

Example 5-D1 (racemic diastereomer 1) was separated into its enantiomers using a 2×25 cm Chiralcel OJ column eluting with 15% ethanol in heptane with a flow rate of 15 ml/min to yield Example 5-D1E1 (enantiomer 1 of diastereomer 1) eluting around 6 min and Example 5-D1E2 (enantiomer 2 of diastereomer 1) around 9 min.

Example 5-D1E1 (Enantiomer 1 of Diastereomer 1)

Analytical chiral HPLC (25×0.46 cm Chiralcel OJ column, 15% ethanol in heptane eluting at 1 ml/min): retention time 4.77 min This enantiomer was further purified by application to a 2 g silica SPE cartridge eluting with heptane followed by 0 to 25% diethylether in cyclohexane gradient.
LCMS: MH$^+$ 443
$^{19}$F—NMR: (CDCl$_3$) −80.37

Example 5-D1E2 (Enantiomer 2 of Diastereomer 1)

Analytical chiral HPLC (25×0.46 cm Chiralcel OJ column, 15% ethanol in heptane eluting at 1 ml/min): retention time 7.83 min
LCMS: MH$^+$ 443
$^{19}$F—NMR: (CDCl$_3$) −80.38

Example 5-D2 (racemic diastereomer 2) was separated into its enantiomers using a 2×25 cm Chiralpak AD column eluting with 5% ethanol in heptane with a flow rate of 15 ml/min. Example 5-D2E1 (enantiomer 1 of diastereomer 2) eluting around 8.5 min and Example 5-D2E2 (enantiomer 2 of diastereomer 2) around 10.5 min.

Example 5-D2E1 (Enantiomer 1 of Diastereomer 2)

Analytical chiral HPLC (25×0.46 cm Chiralpak AD column, 5% ethanol in heptane eluting at 1 ml/min): retention time 6.12 min
LCMS: MH$^+$ 443
$^{19}$F—NMR: (CDCl$_3$) −81.21

Example 5-D2E2 (Enantiomer 2 of Diastereomer 2)

Analytical chiral HPLC (25×0.46 cm Chiralpak AD column, 5% ethanol in heptane eluting at 1 ml/min): retention time 7.30 min
LCMS: MH$^+$ 443
$^{19}$F—NMR: (CDCl$_3$) −81.21

Example 6

3-(1-Ethyl-1,2,3,4-tetrahydro-1-naphthalenyl)-1,1,1-trifluoro-2-[(5-guinolinylamino)methyl]-2-propanol A solution of 2-[(1-ethyl-1,2,3,4-tetrahydro-1-naphthalenyl)methyl]-2-(trifluoromethyl)oxirane (D1, racemic diastereomer 1) (Intermediate 14) (150 mg, 0.53 mmol), 5-quinolinamine (92 mg, 0.64 mmol) and potassium tert-butoxide (72 mg, 0.64 mmol) in dry N,N-dimethylformamide (4 ml) was stirred for 16 h under a nitrogen atmosphere. The mixture was then poured into water and extracted with ethyl acetate. The organic extracts were washed with brine, dried over anhydrous sodium sulphate and evaporated. Purification by flash chromatography on silica (eluent pentane/ethyl acetate 4:1) gave Example 6-D1 (racemic diastereomer 1) as an orange solid (16 mg).

Similar reaction of 2-[(1-ethyl-1,2,3,4-tetrahydro-1-naphthalenyl)methyl]-2-(trifluoromethyl)oxirane (racemic diastereomer 2) (Intermediate 15) with 5-quinolinamine afforded Example 6-D2 (racemic diastereomer 2).

Example 6-D1 (Racemic Diastereomer 1)

LCMS: retention time 3.40 min, MH$^+$ 429

Example 6-D2 (Racemic Diastereomer 2)

LCMS retention time 3.45 min, MH$^+$ 443

Biological Experimental

Glucocorticoid Receptor Binding Assay

The ability of compounds to bind to the glucocorticoid receptor was determined by assessing their ability to compete with fluorescent-labelled glucocortioid using a kit supplied by PanVera (Madison, Wis., USA) or using in house reagents. Compounds were solvated and diluted in DMSO, and transferred directly into assay plates. Fluorescent glucocorticoid and partially purified glucocorticoid receptor with a stabilisation peptide were added to the plates and incubated at 22° C. for 2 hours in the dark. Binding of the compound was assessed by analysing the displacement of fluorescent ligand by measuring the decrease in fluorescence polarisation signal from the mixture.

The pIC$_{50}$ values for compounds of Examples 1-D1, 1-D1E1, 1-D2, 2-D1, 2D1-E1, 2-D2, 2-D2E1, 3-D1, 3-D1E2, 3-D2, 3-D2E1, 3-D2E2, 4-D1, 4-D1E2, 4-D2, 5-D1, 5-D1E1, 5-2, 5-D2E1, 6-D1 and 6-D2 are >7 for the glucocorticoid receptor binding assay.

Glucocorticoid mediated Transrepression of NFkB activity.

Human A549 lung epithelial cells were engineered to contain a secreted placental alkaline phosphatase gene under the control of the distal region of the NFkB dependent ELAM promoter as previously described in Ray, K. P., Farrow, S., Daly, M., Talabot, F. and Searle, N. "Induction of the E-selectin promoter by interleukin 1 and tumour necrosis factor alpha, and inhibition by glucocorticoids" *Biochemical Journal*. 1997 328 707-15.

Compounds were solvated and diluted in DMSO, and transferred directly into assay plates such that the final concentration of DMSO was 0.7%. Following the addition of cells (40K per well), plates were incubated for 1 hr prior to the addition of 3 ng/ml human recombinant TNFα. Following continued incubation for 16 hours, alkaline phosphatase activity was determined by measuring the change in optical density at 405 nM with time following the addition of 0.7 volumes of assay buffer (1 mg/ml p-nitrophenylphosphate dissolved in 1 M diethanolamine, 0.28M NaCl, 0.5 mM MgCl$_2$).

The pIC$_{50}$ values for Examples 1-D1, 1-D1E1, 2-D1, 2-D1E1, 2-D2E1, 3-D1, 3-D1E2, 3-D2E1, 4-D1, 4-D1E2, 5-D1, 5-D1E1 and 6-D1 are >7.5 for the NFkB assay.

Glucocorticoid Mediated Transactivation of MMTV Driven Gene Expression

Human A549 lung epithelial cells or human MG63 osteosarcoma were engineered to contain a renialla luciferase gene under the control of the distal region of the LTR from the mouse mammary tumour virus as previously described (Austin, R. H., Maschera, B., Walker, A., Fairbairn, L., Meldrum, E., Farrow, S. and Uings, I. J. Mometasone furoate is a less specific glucocorticoid than fluticasone propionate. *European Respiratory Journal* 2002 20 1386-1392).

Compounds were solvated and diluted in DMSO, and transferred directly into assay plates such that the final concentration of DMSO was 0.7%. Following the addition of cells (40K per well), plates were incubated for 6 hr. Luciferase activity was determined using the Firelight kit (Packard, Pangbourne, UK).

The Examples 1-D1, 1-D1E1, 2-D1, 2-D1E1, 2-D2, 2-D2E1, 2-D2E2, 3-D1, 3-D1E2, 3-D2, 3-D2E1, 4-D1, 4-D1E2, 5-D1, 5-D1E1, 5-D2, 5-D2E1 and 6-D1 all have reduced efficacy in the MMTV transactivation assay compared to the NFkB assay Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

What is claimed is:
1. A compound of formula (I):

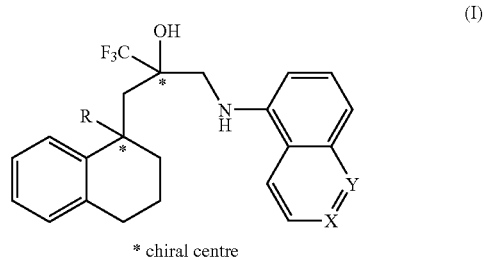

* chiral centre wherein
R represents a methyl or an ethyl group
X represents N, C—H or C—CH$_3$ with the proviso that when X represents C—H or C—CH$_3$, Y represents N and when X represents N, Y represents C—H
or a physiologically functional compound thereof.

2. A compound of formula (I):

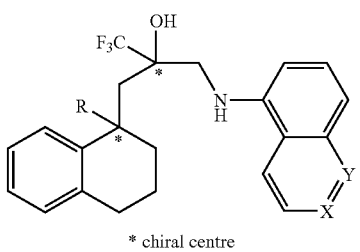

* chiral centre wherein
R represents a methyl or an ethyl group
X represents N, C—H or C—CH₃ with the proviso that when X represents C—H or C—C—H₃, Y represents N and when X represents N, Y represents C—H.

3. A compound as claimed in claim 1 wherein R represents a methyl group.

4. A compound as claimed in claim 1 wherein R represents an ethyl group.

5. A compound as claimed in claim 1 wherein X represents a C—H group.

6. A compound as claimed in claim 1 wherein X represents a C—CH₃ group.

7. A compound as claimed in claim 1 wherein X represents N.

8. A compound as claimed in claim 1 which is the diastereomer D1 of the compound of formula (I).

9. A compound as claimed in claim 1 which is the isomer D1E1 of the compound of formula (I).

10. A compound as claimed in claim 1 which is the isomer D1E2 of the compound of formula (I).

11. A compound which is:
1,1,1-Trifluoro-3-(1-methyl-1,2,3,4-tetrahydro-1-naphthalenyl)-2-[(5-quinolinylamino)methyl]-2-propanol D1;
1,1,1-Trifluoro-3-[(2-methyl-5-quinolinyl)amino]-2-[(1-methyl-1,2,3,4-tetrahydro-1-naphthalenyl)methyl]-2-propanol D1;
1,1,1-Trifluoro-3-(5-isoquinolinylamino)-2-[(1-methyl-1,2,3,4-tetrahydro-1-naphthalenyl)methyl]-2-propanol D1;
3-(1-Ethyl-1,2,3,4-tetrahydro-1-naphthalenyl)-1,1,1-trifluoro-2-[(5-isoquinolinylamino)methyl]-2-propanol D1;
3-(1-Ethyl-1,2,3,4-tetrahydro-1-naphthalenyl)-1,1,1-trifluoro-2-{[(2-methyl-5-quinolinyl)amino]methyl}-2-propanol D1;
3-(1-Ethyl-1,2,3,4-tetrahydro-1-naphthalenyl)-1,1,1-trifluoro-2-{[(2-methyl-5-quinolinyl)amino]methyl}-2-propanol D1E1;
3-(1-Ethyl-1,2,3,4-tetrahydro-1-naphthalenyl)-1,1,1-trifluoro-2-[(5-quinolinylamino)methyl]-2-propanol D1; or
a physiologically functional compound thereof.

12. A compound which is:
1,1,1-Trifluoro-3-(1-methyl-1,2,3,4-tetrahydro-1-naphthalenyl)-2-[(5-quinolinylamino)methyl]-2-propanol D1E1;
1,1,1-Trifluoro-3-[(2-methyl-5-quinolinyl)amino]-2-[(1-methyl-1,2,3,4-tetrahydro-1-naphthalenyl)methyl]-2-propanol D1E1;
1,1,1-Trifluoro-3-(5-isoquinolinylamino)-2-[(1-methyl-1,2,3,4-tetrahydro-1-naphthalenyl)methyl]-2-propanol D1E2;
3-(1-Ethyl-1,2,3,4-tetrahydro-1-naphthalenyl)-1,1,1-trifluoro-2-[(5-isoquinolinylamino)methyl]-2-propanol D1E2;
3-(1-Ethyl-1,2,3,4-tetrahydro-1-naphthalenyl)-1,1,1-trifluoro-2-{[(2-methyl-5-quinolinyl)amino]methyl}-2-propanol D1E1; or
a physiologically functional compound derivative thereof.

13. A compound which is:
1,1,1-Trifluoro-3-[(2-methyl-5-quinolinyl)amino]-2-[(1-methyl-1,2,3,4-tetrahydro-1-naphthalenyl)methyl]-2-propanol D1E1;
1,1,1-Trifluoro-3-(5-isoquinolinylamino)-2-[(1-methyl-1,2,3,4-tetrahydro-1-naphthalenyl)methyl]-2-propanol D1E2; or
a physiologically functional compound thereof.

14. A pharmaceutical composition comprising a compound as claimed in claim 1, or a physiologically functional compound thereof, in admixture with one or more physiologically acceptable diluents or carriers.

15. A pharmaceutical aerosol formulation comprising a compound of formula (I) as claimed in claim 1, or a physiologically functional compound thereof, and a fluorocarbon or hydrogen-containing chlorofluorocarbon as propellant, optionally in combination with one or more components selected from the group consisting of a surfactant and a cosolvent.

16. A pharmaceutical formulation as claimed in claim 15 wherein the propellant is selected from the group consisting of 1,1,1,2-tetrafluoroethane, 1,1,1,2,3,3,3-heptafluoro-n-propane and mixtures thereof.

17. A combination comprising a compound as claimed in claim 1, or a physiologically functional compound thereof, together with one or more other therapeutically active agents.

18. A combination according to claim 17 in which said therapeutically active agent is a β₂-adrenoreceptor agonist.

19. A combination according to claim 17 in which said therapeutically active agent is a PDE4 inhibitor.

20. A process for the preparation of a compound of formula (I) as claimed in claim 1, or a physiologically functional compound, comprising reacting an epoxide of formula (II):

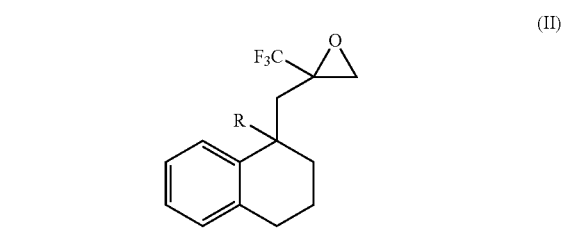

Wherein R represents a methyl or ethyl group
With a quinolinamine or isoquinolinamine of formula (III):

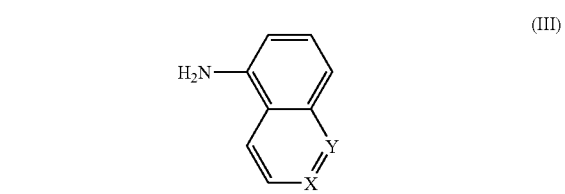

Wherein X and Y are as defined above for the compounds of formula (I).

* * * * *